US011807598B2

(12) United States Patent
Contractor et al.

(10) Patent No.: US 11,807,598 B2
(45) Date of Patent: Nov. 7, 2023

(54) PROCESS FOR PREPARING FATTY ACID CHLORIDES AND N-ACYL AMINO ACID SALTS

(71) Applicants: Clariant International Ltd., Muttenz (CH); Transpek Industry Limited, Gujarat (IN)

(72) Inventors: Prerak Rajendrakumar Contractor, Singapore (SG); Raju Dayaram Patil, Gujarat (SG); Jignalkumar Nurpeshkumar Soni, Gujarat (SG)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

(21) Appl. No.: 17/290,502

(22) PCT Filed: Oct. 30, 2019

(86) PCT No.: PCT/EP2019/079715
§ 371 (c)(1),
(2) Date: Apr. 30, 2021

(87) PCT Pub. No.: WO2020/089326
PCT Pub. Date: May 7, 2020

(65) Prior Publication Data
US 2021/0380520 A1 Dec. 9, 2021

(30) Foreign Application Priority Data
Oct. 31, 2018 (IN) .............................. 201811041255

(51) Int. Cl.
C07C 51/60 (2006.01)
A61K 8/44 (2006.01)

(52) U.S. Cl.
CPC ............... C07C 51/60 (2013.01); A61K 8/44 (2013.01); A61K 2800/10 (2013.01); A61K 2800/805 (2013.01)

(58) Field of Classification Search
None
See application file for complete search history.

(56) References Cited

U.S. PATENT DOCUMENTS

| 5,166,427 A | 11/1992 | Hohmann |
| 5,200,560 A | 4/1993 | Kahl |
| 5,247,105 A | 9/1993 | Evans |
| 5,278,328 A | 1/1994 | Endo |
| 5,430,186 A | 7/1995 | Ksoll |
| 5,623,082 A | 4/1997 | Decker |
| 6,569,829 B1 | 5/2003 | Yamawaki |
| 6,703,517 B2 | 3/2004 | Hattori |
| 2005/0085651 A1 | 4/2005 | Kitamura |
| 2010/0273879 A1* | 10/2010 | Klug ............. A61Q 19/00 554/68 |
| 2012/0090983 A1* | 4/2012 | Krull ............. H05B 6/701 204/157.81 |
| 2015/0141682 A1* | 5/2015 | Koshti ............. C07C 51/60 554/37 |
| 2017/0274362 A1 | 9/2017 | Koshti |

FOREIGN PATENT DOCUMENTS

| CN | 1907971 | | 2/2007 | |
| CN | 105601502 | * | 5/2016 | ............. C07C 51/60 |
| CN | 105669436 | * | 6/2016 | ........... C07C 201/12 |
| DE | 2234009 | | 1/1974 | |

OTHER PUBLICATIONS

International Search Report for App. No. PCT/EP2019/079715, dated Jan. 28, 2020, 10 pages.

* cited by examiner

Primary Examiner — Amy C Bonaparte
(74) Attorney, Agent, or Firm — Tod A. Waldrop

(57) ABSTRACT

The invention relates to a process for preparing fatty acid chlorides. In a subsequent step, the fatty acid chlorides can be used to prepare N-acyl amino acid salts. The process comprises the formation of a fatty acid chloride in an amine catalyzed reaction of a fatty acid with phosphorous trichloride, thionyl chloride or phosgene, preferably thionyl chloride. The process for preparing N-acyl amino acid salts further comprises the reaction of the fatty acid chloride with an amino acid or an amino ethane sulfonic acid.

26 Claims, No Drawings

PROCESS FOR PREPARING FATTY ACID CHLORIDES AND N-ACYL AMINO ACID SALTS

FIELD OF THE INVENTION

The invention relates to a process for preparing fatty acid chlorides. In a subsequent step, the fatty acid chlorides can be used to prepare N-acyl amino acid salts. The process comprises the formation of a fatty acid chloride in an amine catalyzed reaction of a fatty acid with phosphorous trichloride, thionyl chloride or phosgene, preferably thionyl chloride. The process for preparing N-acyl amino acid salts further comprises the reaction of the fatty acid chloride with an amino acid or an amino ethane sulfonic acid.

BACKGROUND OF THE INVENTION

N-Acyl amino acid salts are widely used as surfactants in many applications. They are known as being particularly mild anionic surfactants useful for personal care applications. For example, surfactants like sodium lauroyl sarcosinate, sodium myristoyl sarcosinate, sodium cocoyl glycinate, sodium cocoyl N-methyl taurate are commercially used in face washes, body washes since they exhibit good cleansing power and are milder to skin and hair compared to other anionic surfactants. Alkanoyl sarcosinates find applications in mouth washes and in dentifrices, in general, due to their bacteriostatic activity.

In the manufacture of N-acyl amino acid salts, a fatty acid or a mixture of fatty acids is reacted with the amino functionality of an amino acid through the intermediacy of fatty acid chloride under Schotten Baumann conditions. The Schotten-Baumann condensation between a fatty acid chloride and an amino acid is typically done under basic aqueous conditions, optionally in mixed solvent systems comprising organic solvent and water (U.S. Pat. Nos. 6,703,517, 6,569,829 and US 2005/0085651).

The intermediates of the process, i.e., the fatty acid chlorides, can be manufactured by reacting fatty acids and a halogenating agent, like phosphorous trichloride, phosgene or thionyl chloride. The chlorination is typically catalyzed by N,N-dimethyl formamide (DMF). DMF or similar substituted formamides can form a complex (Vilsmeier complex) with $COCl_2$ or $SOCl_2$ which is the actual catalytic species (U.S. Pat. Nos. 5,430,186; 5,623,082; 5,200,560; 5,278,328 and 5,166,427) in the chlorination of acids.

The disadvantages and complications of this process arise out of the presence of the dark colored Vilsmeier complex in the product and the difficulty of complete separation of said complex from the product. Many attempts have been made towards improving 'phase-separation', i.e., separating the complex phase from the product phase. While major portion of the Vilsmeier compounds and the remaining DMF are separated out on the completion of the reaction by allowing the phases to separate, complete removal by either phase separation, or fractionation/distillation entails additional processing and loss of yield of valuable product. The same problems arise from the use of other formamides and acetamides.

Another serious concern is the toxicity and health hazard associated with formamides, in particular DMF. For use in personal care applications, complete removal therefore needs to be ensured. Thus, fatty acid chlorides made by halogenating fatty acids with phosphorous trichloride, phosgene or thionyl chloride using formamides, acetamides, or any other analogues as catalysts, need additional steps of purifications resulting in significant loss of yield, higher energy consumption and longer batch cycle time resulting into lower productivity.

While there are methods known in the art, e.g., from EP 2 888 226 B1, which avoid DMF as a catalyst, these methods are insufficient regarding the purity, the conversion and the color of the final product.

As a result, there is a need to significantly improve the manufacturing process of fatty acid chlorides, to improve product quality and quantitative yield, to increase product purity and conversion, to improve the color properties of the product, to reduce reaction and batch cycle times, and to minimize product losses due to purification steps.

The present invention relates to a process of producing fatty acid chlorides of high quality and with quantitative yield. The process according to the present invention is carried out at significantly reduced batch times, low energy consumption, with minimum wastage, and high cost-efficacy (low energy consumption, minimum purification steps), and is efficient (faster rate of catalysis). The process according to the present invention further avoids using toxic catalysts and is applicable for making surfactants for personal care applications.

SUMMARY OF THE INVENTION

The present invention relates to a process for preparing a fatty acid chloride of formula R—COCl, wherein R is a linear or branched, saturated alkyl group having from 6 to 30 carbon atoms, or a linear or branched, mono- or polyunsaturated alkenyl group having from 6 to 30 carbon atoms, wherein the process comprises
i. providing a fatty acid of formula R—COOH, and
ii. reacting the fatty acid of step i. with phosphorous trichloride, thionyl chloride or phosgene, preferably thionyl chloride, in the presence of a catalyst to form a fatty acid chloride of formula R—COCl, wherein the catalyst is an amine.

The present invention further relates to a process for preparing an N-acyl amino acid salt of formula (I)

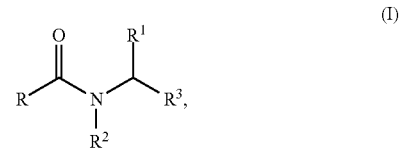

wherein
R is a linear or branched, saturated alkyl group having from 6 to 30 carbon atoms, or a linear or branched, mono- or polyunsaturated alkenyl group having from 6 to 30 carbon atoms,
$R^1$ is selected from the residues on the α-carbon of natural α-amino acids,
$R^2$ is H or an alkyl group with 1 to 4 carbon atoms,
$R^3$ is selected from COOQ and $CH_2$—$SO_3Q$, and
Q stands for a single cation or two or more different cations,
wherein the method comprises
i. providing a fatty acid of formula R—COOH,
ii. reacting the fatty acid of step i. with phosphorous trichloride, thionyl chloride or phosgene, preferably thionyl chloride, in the presence of a catalyst to form a fatty acid chloride of formula R—COCl, wherein the catalyst is an amine; and iii. reacting the fatty acid chloride of step ii. with a compound of formula (II)

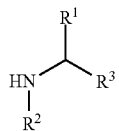
(II)

to form the N-acyl amino acid salt of formula (I), wherein step iii. is carried out in water, and in the presence of a base providing cations Q, The present invention further relates to a process for preparing a personal care composition comprising
A) preparing an N-acyl amino acid salt of formula (I) according to the process of the invention; and
B) formulating the N-acyl amino acid salt of formula (I) into a composition comprising a cosmetically acceptable carrier and at least one cosmetic benefit agent to form a personal care composition.

The present invention further relates to an N-acyl amino acid salt of formula (I) obtained according to the process of the invention.

DETAILED DESCRIPTION OF THE INVENTION

The present invention relates to a process for preparing a fatty acid chloride of formula R—COCl, wherein R is a linear or branched, saturated alkyl group having from 6 to 30 carbon atoms, or a linear or branched, mono- or polyunsaturated alkenyl group having from 6 to 30 carbon atoms, wherein the process comprises
i. providing a fatty acid of formula R—COOH, and
ii. reacting the fatty acid of step i. with phosphorous trichloride, thionyl chloride or phosgene, preferably thionyl chloride, in the presence of a catalyst to form a fatty acid chloride of formula R—COCl, wherein the catalyst is an amine.

The present invention further relates to a process for preparing an N-acyl amino acid salt of formula (I)

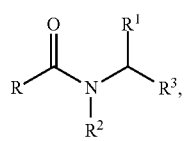
(I)

wherein
R is a linear or branched, saturated alkyl group having from 6 to 30 carbon atoms, or a linear or branched, mono- or polyunsaturated alkenyl group having from 6 to 30 carbon atoms,
$R^1$ is selected from the residues on the α-carbon of natural α-amino acids,
$R^2$ is H or an alkyl group with 1 to 4 carbon atoms,
$R^3$ is selected from COOQ and $CH_2$—$SO_3Q$, and
Q is a cation or a combination of more than one cation, wherein the method comprises
i. providing a fatty acid of formula R—COOH,
ii. reacting the fatty acid of step i. with phosphorous trichloride, thionyl chloride or phosgene, preferably thionyl chloride, in the presence of a catalyst to form a fatty acid chloride of formula R—COCl, wherein the catalyst is an amine; and
iii. reacting the fatty acid chloride of step ii. with a compound of formula (II)

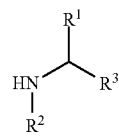
(II)

to form the N-acyl amino acid salt of formula (I), wherein step iii. is carried out in water, and in the presence of a base providing cations Q.

The following description and preferred embodiments, in particular regarding the compounds and the process steps i. and ii., are applicable to and suitable for the process of preparing a fatty acid chloride and for the process of preparing an N-acyl amino acid salt of formula (I).

Formula (I)

The N-acyl amino acid salt formed according to the present invention is of formula (I)

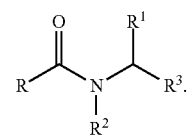
(I)

R is a linear or branched, saturated alkyl group having 6 to 30 carbon atoms, preferably 8 to 22 carbon atoms, more preferably 12 to 18 carbon atoms, or a linear or branched, mono- or polyunsaturated alkenyl group having 6 to 30 carbon atoms, preferably 8 to 22 carbon atoms, more preferably 12 to 18 carbon atoms.

R is preferably linear.

The alkyl or alkenyl groups may be derived from fatty acids that occur in nature, e.g., in the form of animal fats or vegetable oils.

The unsaturated alkenyl groups may have 1 to 6 double bonds, preferably 1 to 3 double bonds, more preferably 1 double bond or two double bonds or three double bonds. The unsaturated alkenyl groups are preferably derived from oleic acid, recinoleic acid, linolic acid, linolenic acid, eleosteric acid, eicosenoic acid, euritic acid, docosadienoic acid and undecylenic acid, or a combination thereof.

The saturated alkyl groups are preferably derived from palm/palm kernel oil or coconut oil, Preferably, the saturated alkyl groups are even numbered. They preferably range from octanoic acid (C8) to stearic acid (C18). Fatty acids with higher numbers of carbons (C18 to C22) are preferably derived from mustard oil, tung oil and rapeseed oil. It may be preferred that R is derived from lauric acid, tridecanoid acid, myristic acid, pentadecanoic acid, palmitic acid, heptadecanoic acid, stearic acid, or a combination thereof. More preferably, R is derived from lauric acid, myristic acid, palmitic acid, and stearic acid, or a combination thereof.

$R^1$ is selected from the residues on the α-carbon of natural α-amino acids.

Natural amino acids are the amino acids Glycine, Alanine, Valine, Leucine, Isoleucine, Methionine, Proline, Cystein, Phenyl alanine, Tyrosine, Tryptophan, Arginine, Lysine, Histidine, Aspartic acid, Glutamic acid, Serine, Threonine, Asparagine, and Glutamine.

$R^1$ is preferably selected from H, —$CH_3$, —$CH(CH_3)_2$, —$CH_2CH(CH_3)_2$, —$CH(CH_3)CH_2CH_3$, —$(CH_2)_2SCH_3$, —$CH_2SH$,

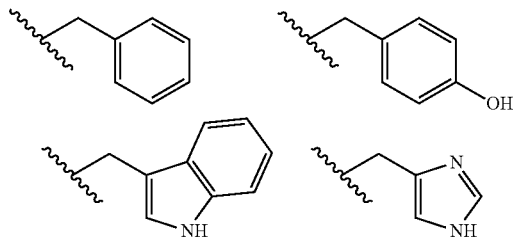

—$(CH_2)_3NHC(NH)(NH_2)$, —$(CH_2)_4NH_2$, —$CH_2COOH$, —$(CH_2)_2COOH$, —$CH_2OH$, —$CH(OH)CH_3$, —$CH_2CONH_2$, —$(CH_2)_2CONH_2$. More preferably, $R^1$ is H.

Q is a cation or a combination of more than one cation, preferably a monovalent cation or a combination of more than one monovalent cation. According to the present invention, Q may for example be selected from alkali metal cations and ammonium cation. Preferred alkali metal cations are $Li^+$, $Na^+$ and $K^+$. Suitable ammonium cations may be of formula $[HNR^2_3]^+$ wherein each $R^2$ is independently from each other selected from H and alkyl with 1 to 6 carbon atoms, for example H, methyl and ethyl, preferably $NH_4^+$. Most preferred cations Q according to the present invention are $Na^+$ and $K^+$.

Step i.

According to the present invention, a fatty acid of formula R—COOH is provided in step i. Therein, the group R is defined as above for the compounds of formula (I).

Preferred unsaturated fatty acids are oleic acid, recinoleic acid, linolic acid, linolenic acid, eleosteric acid, eicosenoic acid, euritic acid, docosadienoic acid and undecylenic acid, or a combination thereof.

Preferred saturated fatty acids are derived from palm/palm kernel oil or coconut oil. Preferred saturated fatty acids are even numbered. They preferably range from octanoic acid (C8) to stearic acid (C18). Fatty acids with higher numbers of carbons (C18 to C22) are preferably derived from mustard oil, tung oil and rapeseed oil. For example, the fatty acid is selected from lauric acid, tridecanoid acid, myristic acid, pentadecanoic acid, palmitic acid, heptadecanoic acid, stearic acid, or a combination thereof. More preferably, the fatty acid is lauric acid, myristic acid, palmitic acid, and stearic acid, or a combination thereof.

Step ii.

According to the present invention, the fatty acid of formula R—COOH provided in step i. is reacted with phosphorous trichloride, thionyl chloride or phosgene, preferably thionyl chloride, in the presence of a catalyst to form a fatty acid chloride of formula R—COCl.

The group R of the fatty acid chloride R—COCl is defined as above for the compounds of formula (I).

According to the present invention, the catalyst is an amine.

Amines suitable for the present invention are compounds having a primary or secondary amino group. Amines can optionally have at least one additional functional group.

Preferably, the amines have at least one acidic functional group. Acidic functional groups according to the present invention encompass acid groups and the respective deprotonated form of the group, i.e., its salt. For example, acidic functional groups are carboxylic acid groups, sulfur-based acidic groups, like —$SO_3H$, —$SO_2H$, and phosphorous-bases acidic groups, like —$PO_3H_2$, —$PO_2H$, —O—$PO_3H_2$, —O—$PO_2H$, and the respective salts, e.g., —COOX, $SO_3X$, $SO_2X$, —$PO_3X$, —$PO_2X$, —O—$PO_3HX$, —O—$PO_2X$, with X being a cation, preferably selected from alkali metal cations, earth alkali metal cations and ammonium cations, more preferably X is Q. According to the present invention, amines having an amino group and a carboxylic acid functional group, or its salt are amino acids.

Amino acids can be natural and non-natural amino acids. Natural amino acids are the amino acids Alanine, Valine, Leucine, Isoleucine, Methionine, Proline, Cystein, Phenyl alanine, Tyrosine, Tryptophan, Arginine, Lysine, Histidine, Aspartic acid, Glutamic acid, Serine, Threonine, Asparagine, and Glutamine, all having L-stereochemistry at the α-carbon, and Glycine. Non-natural amino acids are amino acids that do not fall within the group of natural amino acids. Preferred non-natural amino acids are D-isomers of the natural amino acids, or mixtures of stereoisomers of the natural amino acids.

Preferably, the amine used in step ii. is selected from amino acids and amino ethane sulfonic acids. It may be preferred that the amine used in step ii. is a compound of formula (II)

with $R^1$, $R^2$, and $R^3$ as defined above.

According to the invention, it is preferred that the amine used in step ii. is selected from natural amino acids, taurine and N-methyl taurine, and salts thereof. More preferably, the amine used in step ii. is selected from glycine, taurine and N-methyl taurine.

According to the present invention, the amine used in step ii. of the claimed process can be a combination of two or more amines. Preferably, the amine is glycine, taurine, N-methyl taurine, or a combination thereof. For example, the amine is a combination of glycine and taurine, or a combination of glycine and N-methyl taurine, or a combination of taurine and N-methyl taurine, or a combination of glycine, taurine and N-methyl taurine.

It is preferred according to the present invention that the compound of formula (II) used in step iii. of the process is the same as the amine used as the catalyst used in step ii. Thereby, at least one of the purity of the product, the color properties, and the yield can be further improved.

The process, in particular step ii., is carried out in the absence of DMF, preferably in the absence of formamides and acetamides. According to the present invention, the term "absence of" a compound means that said compound is not intentionally added to the process, whereas said compound may be formed in as an intermediate or side product while carrying out the process. During the process traces of formamides and acetamides may be formed. Preferably, no more than 1 wt.-% of formamides and acetamides are comprised at any time during the process, based on the total weight of fatty acid. For example, no more than 1 wt.-% or 0.001 to 0.8 wt.-% or 0.01 to 0.5 wt.-% or 0.01 to 0.1 wt.-% or 0 to 0.1 wt.-% or 0 to 0.01 wt.-% of formamides and acetamides are comprised at any time during the process, based on the total weight of fatty acid. Preferably, the term "absence of" a compound means that said compound is not intentionally added to the process and is not formed in as an intermediate or side product while carrying out the process.

The fatty acid of step i. is converted to the corresponding acid chloride by treating them with phosphorous trichloride, thionyl chloride or phosgene, preferably thionyl chloride.

According to the present invention, step ii. is carried out with an excess of phosphorous trichloride, thionyl chloride or phosgene, preferably thionyl chloride, of at least 5%, based on the stoichiometric amount of the fatty acid. Preferably, step ii. is carried our with an excess of phosphorous trichloride, thionyl chloride or phosgene, preferably thionyl chloride, of from 5 to 25%, for example from 6 to 20%, or from 7 to 15%, more preferably from 7 to 10%, the percentages based on the stoichiometric amount of the fatty acid.

According to the present invention, step ii. is carried out in the presence of more than 0.5% of catalyst, based on the total weight of the fatty acid. Preferably, step ii. is carried out in the presence of from more than 0.5 to 10% of catalyst, for example from 1 to 7%, or from 2.1 to 5%, or from 2.3 to 4%, more preferably from 2.5 to 3% of catalyst, the percentages based on the total weight of the fatty acid.

According to the present invention, the halogenation of the fatty acids with phosphorous trichloride, thionyl chloride or phosgene, preferably thionyl chloride, is carried out at a temperature of from 30° C. to 65° C., preferably at a temperature of from 40° C. to 65° C., more preferably at a temperature of from 50 to 60° C., most preferably at 55 to 60° C. The high reaction temperature (halogenation temperature) provides fast reaction and batch cycle times. The process is temperature stable.

Preferably, step ii. is carried out at a temperature of from 30° C. to 65° C., with an excess of phosphorous trichloride, thionyl chloride or phosgene of at least 5%, based on the total weight of the fatty acid, and in the presence of more than 0.5% of catalyst, based on the total weight of the fatty acid.

It may be preferred that the phosphorous trichloride, thionyl chloride or phosgene, preferably thionyl chloride, be added to the fatty acid at a lower temperature, e.g., at a temperature of from 20 to 50° C., or at a temperature of from 25 to 40° C. In this case, the reaction mixture is preferably heated to the halogenation temperature as defined above only after complete addition of the phosphorous trichloride, thionyl chloride or phosgene, preferably thionyl chloride.

The halogenation temperature is maintained until the reaction is complete. Completion of the halogenation can be determined by gas chromatography.

Step ii. of the process is preferably carried out under inert gas conditions, for examples under a nitrogen or argon blanket.

To avoid side reactions, the gaseous by-products HCl and $SO_2$ need to be removed from the reaction system. For example, step ii. is carried out under a inert gas conditions in conjunction with a scrubbing system for absorption of HCl and $SO_2$. Also a 'closed loop' technique can be followed where $SO_2$ and HCl are separated from the reaction mixture and converted to $SOCl_2$.

Step iii.

According to the present invention, the fatty acid chloride of step ii. is reacted with a compound of formula (II) to form the N-acyl amino acid salt of formula (I).

The reaction in step iii. is a Schotten-Baumann reaction which is carried out under Schotten-Baumann conditions. In general the Schotten-Baumann reaction is the reaction of an amine with an organic acid chloride in water and in the presence of a base to make the respective amide. Accordingly, step iii. is carried out in water and in the presence of a base.

The base used in step iii. of the present invention is a base providing Q as cations. The base may be selected from water-soluble inorganic bases and water-soluble organic amine bases. Suitable bases are for example alkali and earth alkali metal hydroxides, alkali and earth alkali metal carbonates, and amines; for example alkali metal hydroxides, alkali metal carbonates, and amines. Preferred alkali metal hydroxides are LiOH, NaOH and KOH. Preferred alkali metal carbonates are $Li_2CO_3$, $Na_2CO_3$ and $K_2CO_3$. Preferred amines are of formula $N(R^2)_3$ with $R^2$ being dependently from each other selected from H and alkyl groups with 1 to 6 carbon atoms, e.g., $NH_3$, $NMe_3$, and $NEt_3$, preferably $NH_3$. According to the present invention, the preferred base is an alkali metal hydroxide, more preferably NaOH, KOH or a combination thereof.

In the compound of formula (II)

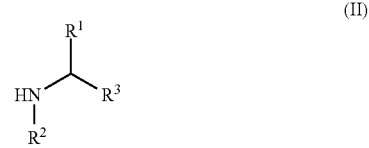

(II)

used in step iii., $R^1$, $R^2$, and $R^3$ are as defined above.

Suitable compounds of formula (II) used in step iii. are therefore amino acids and amino ethane sulfonic acids, for example natural amino acids and non-natural amino acids, taurine and N-methyl taurine. Natural amino acids are the amino acids Alanine, Valine, Leucine, Isoleucine, Methionine, Proline, Cystein, Phenyl alanine, Tyrosine, Tryptophan, Arginine, Lysine, Histidine, Aspartic acid, Glutamic acid, Serine, Threonine, Asparagine, and Glutamine, all having L-stereochemistry at the α-carbon, and Glycine. Non-natural amino acids suitable for the present invention are selected from the respective amino acids having D-stereochemistry at the α-carbon, i.e., D-Alanine, D-Valine, D-Leucine, D-Isoleucine, D-Methionine, D-Proline, D-Cystein, D-Phenyl alanine, D-Tyrosine, D-Tryptophan, D-Arginine, D-Lysine, D-Histidine, D-Aspartic acid, D-Glutamic acid, D-Serine, D-Threonine, D-Asparagine, and D-Glutamine. In step iii. of the present invention, combinations of compounds of formula (II), e.g., of amino acids and amino ethane sulfonic acids, can also be used. It is preferred according to the present invention that the compound of formula (II) used in step iii. is glycine, taurine, or N-methyl taurine.

It can also be preferred that in step iii. combination of two or more compounds of formula (II) is used, e.g., a combination of two or more amino acids, a combination of an amino acid and an amino ethane sulfonic acid, or a combination of two or more amino ethane sulfonic acids is used. For example, a combination of two or more natural amino acids, non-natural amino acids, taurine, N-methyl taurine is used in step iii. Preferably, glycine, taurine, N-methyl taurine, or a combination of two or more thereof is used in step iii.

According to the present invention, the molar ratio of fatty acid chloride to amino acid may be in the range of from 1:1 to 1:1.1. It may be preferred that the molar ratio is in the range of from 1:1 to 1:1.05, more preferably of from 1:1 to 1:1.03.

According to the present invention, step iii. can be carried out at pH 9 to 13. It may be preferred that the pH is in the range of from 10 to 13, more preferably of from 12 to 13. It may also be preferred that step iii. is carried out at pH 10 to 11, e.g., 10.3 to 10.6.

According to the present invention, step iii. can be carried out at a temperature of from 25 to 50° C., preferably at a temperature of from 30° C. to 35° C.

The compounds used in step iii. can be combined in any order. It may be preferred that the amino acid is dissolved in water and the base, and that the fatty acid chloride is added to the amino acid solution. Preferably, the fatty acid chloride is gradually added to the amino acid solution while stirring.

It is preferred according to the present invention that the process is carried out in the absence of organic solvent.

The present invention further relates to a process for preparing a personal care composition. The process comprises A) the preparation of an N-acyl amino acid salt of formula (I), and B) the formulation of the N-acyl amino acid salt of formula (I) into a composition comprising a cosmetically acceptable carrier, and at least one cosmetic benefit agent to form a personal care composition.

Step A), i.e., the preparation of the N-acyl amino acid salt of formula (I), is in accordance with the process described above. The described preferred embodiments also apply.

Through the process for preparing N-acyl amino acid salt of formula (I) according to the invention, it is possible to prepare highly concentrated, salt-containing solutions of the N-acyl amino acid salt of formula (I) having a low content of by-products (for example fatty acid salt), which are monophasic and of low viscosity at 40° C. Such solutions are easy to handle and cost-effective, since there is no need to conduct any separation step. Moreover, no organic reaction solvent is required, which has to be removed and possibly disposed of.

Such solutions comprise an N-acyl amino acid salt of formula (I) as defined above, one or more compounds of formula QCl with Q as defined for formula (I), optionally one or more fatty acid salts of formula R—COOQ with R and Q as defined for formula (I), and water. Preferably, the solution is free of organic solvents. Preferably, the N-acyl amino acid salt of formula (I) is comprised in an amount of from 20 to 30% by weight of the total weight of the solution, for example 23 to 27%. Preferably, QCl is comprised in an amount of from 1 to 8% by weight of the total weight of the solution, for example 2 to 7% or 4 to 6%. Preferably, the fatty acid is comprised in an amount of 0 to 3% by weight of the total weight of the solution, for example 0.01 to 2% or 0.1 to 1.5%.

Step B) comprises formulating the N-acyl amino acid salt of formula (I) into a composition comprising a cosmetically acceptable carrier and at least one cosmetic benefit agent to form a personal care composition. Methods for formulating personal care compositions are commonly known by the skilled person. Any known methods for formulating personal care compositions are suitable, e.g., mixing the components by stirring.

Personal care compositions are compositions intended for topical application to the skin or hair. They may be leave-on formulations (i.e., in which the product is applied topically to the skin or hair and left on for a period of time), or rinse-off formulations (i.e., in which the product is applied topically to the skin or hair and then is subsequently rinsed within minutes from the skin or hair with water, or otherwise wiped off using a substrate with deposition of a portion of the composition). Cosmetically acceptable carriers and cosmetic benefit agents are commonly known by the skilled person. Any known cosmetically acceptable carriers are suitable for the present invention, e.g., water. Cosmetic benefit agents may be compounds that provide a benefit to the skin and/or hair of a consumer. Such benefit may be a cleansing, care or aesthetical benefit, The present invention further relates to an N-acyl amino acid salt of formula (I) obtained according to the process of the present invention.

The process for obtaining the N-acyl amino acid salt of formula (I) is in accordance with the process described above. The described preferred embodiments of the process and of the N-acyl amino acid salt of formula (I) also apply.

Methods

Gas Chromatography 1 g of sample is transferred to a 10 mL volumetric flask containing 5 mL of methylene dichloride. The flask is then filled with methylene dichloride. A sample is injected into the gas chromatograph:

Instrument: 7890 Series GC by Agilent

Column: DB-5 capillary column, 30 m, ID 0.32 mmm, film thickness 0.5 μm

Oven temp.: 120° C.→hold for 2 min→heat to 260° C. with a rate of 10° C./min→hold for 15 min Injector temp.: 270° C.

Detector temp.: 270° C.

Detector: flame ionization detector (FID)

Carrier Gas: Nitrogen

Split ratio: 1:25

Injection amount: 1 μL

Make up gas: Nitrogen

Combustion gas: Hydrogen and air

EXAMPLES

According to examples Ex 1 to Ex 4, lauric acid is reacted with thionyl chloride (TC) in the presence of glycine under the conditions shown in table 1.

According to example CE 1, lauric acid is reacted with thionyl chloride (TC) in the presence of DMF under the conditions shown in table 1.

According to CE 2, lauric acid is reacted with thionyl chloride (TC) in the presence of N-lauroyl glycenic lauric anhydride (anhydride) as the catalyst under the conditions shown in table 1.

According to CE 3, lauric acid is reacted with thionyl chloride (TC) in the presence of N-lauroyl glycenic lauric anhydride under the conditions shown in table 1.

According to CE3 N-lauroyl glycemic lauric anhydride is generated in situ, using sodium lauroyl glycinate.

CE 1-3 are comparative examples.

Amounts are given in grams, percentages are by weight of lauric acid, temperatures are in ° C.

TABLE 1

|  | Ex 1 | Ex 2 | Ex 3 | Ex 4 | CE 1 | CE 2 | CE 3 |
|---|---|---|---|---|---|---|---|
| Raw materials | | | | | | | |
| Amount lauric acid | 1000 | 1000 | 1000 | 1000 | 1000 | 200 | 200 |
| Amount TC | 655 | 637 | 637 | 637 | 655 | 123 | 123 |
| Excess TC | 10% | 7% | 7% | 7% | 10% | 4% | 4% |
| Additional compound | glycine | glycine | glycine | glycine | DMF | anhydride | anhydride |
| Amount additional compound | 10 1% | 30 3% | 20 2% | 10 1% | 10 1% | 0.6 0.3% | 0.6 0.3% |
| Reaction conditions | | | | | | | |
| TC addition time | 35 min | 35 min | 40 min | 40 min | 20 min | 2 h | 2 h |
| TC addition temperature | 36 | 36 | 36 | 36 | 29 | 25 | 25 |
| Reaction time | 4.5 h | 4.75 h | 4.2 h | 4.22 h | 5 h | 4 h | 4 h |
| Reaction temperature | 60 | 60 | 55 | 55 | 55 | 25 | 25 |
| Remaining TC | 5.04 | 3.72 | 4.37 | 3.01 | 3.48 | | |
| Crude weight | 1143 | 1126 | 1146 | 1143 | 1168 | 214 | 218 |
| Results | | | | | | | |
| Purity [%] | 99.33 | 99.69 | 99.73 | 99.72 | 99.1 | 97.4 | 98.5 |
| Acid [%] | 0.22 | 0.134 | 0.054 | 0.09 | 0 | 2.27 | 1.56 |
| Color properties[1] | + | + | + | + | − | + | + |

[1]+: APHA color less than 185; −: APHA color more than 185; APHA color determined according to ASTM D1209

The process is temperature stable. At higher reaction temperatures (e.g., 55 or 60° C.), the cycle time is faster than at room temperature (25° C.), while comparable or even better conversion and purity is obtained. Where the amount of the additional compound is increased from 0.3% as in the CE2 and CE3 to 1-3% as in Ex1-4, the reaction times are shortened, the color is improved, and purity and conversion are increased.

It is shown that high purity products are achievable when replacing DMF by glycine. At the same time very good color properties of the products are achieved for Ex1-4. In contrast, the product of CE1 (which is formed via the dark-colored Vilsmeier complex with DMF) is much darker.

It is shown that the purity of the products of formula (I) is considerably improved when the reaction is carried out at higher reaction temperatures with a higher excess of thionyl chloride and with a higher amount of the additional component than used in CE2 and CE3, while simultaneously the desired color properties are achieved.

Preferred Embodiments of the Invention

A. A process for preparing a fatty acid chloride of formula R—COCl, wherein R is a linear or branched, saturated alkyl group having from 6 to 30 carbon atoms, or a linear or branched, mono- or polyunsaturated alkenyl group having from 6 to 30 carbon atoms, wherein the process comprises
  i. providing a fatty acid of formula R—COOH, and
  ii. reacting the fatty acid of step i. with phosphorous trichloride, thionyl chloride or phosgene, preferably thionyl chloride, in the presence of a catalyst to form a fatty acid chloride of formula R—COCl, wherein the catalyst is an amine.
B. The process of embodiment A, wherein the amine is selected from amino acids and amino ethane sulfonic acids.
C. The process of any one of embodiments A or B, wherein the amine is glycine, taurine or N-methyl taurine.
D. The process of any one of the preceding embodiments, wherein step ii. is carried our with an excess of phosphorous trichloride, thionyl chloride or phosgene, preferably thionyl chloride, of at least 5 wt.-%, based on the stoichiometric amount of fatty acid.
E. The process of any one of the preceding embodiments, wherein step ii. is carried our with an excess of phosphorous trichloride, thionyl chloride or phosgene, preferably thionyl chloride, of from 5 to 25%, based on the stoichiometric amount of fatty acid.
F. The process of any one of the preceding embodiments, wherein step ii. is carried our with an excess of phosphorous trichloride, thionyl chloride or phosgene, preferably thionyl chloride, of from 7 to 10%, based on the stoichiometric amount of fatty acid.
G. The process of any one of the preceding embodiments, wherein step ii. is carried out in the presence of from 0.5 to 10 wt.-% of catalyst, based on the total weight of the fatty acid.
H. The process of any one of the preceding embodiments, wherein step ii. is carried out in the presence of from 2.5 to 3 wt.-% of catalyst, based on the total weight of the fatty acid.
I. The process of any one of the preceding embodiments, wherein step ii. is carried out at a temperature of from 25 to 65° C., preferably of from 30 to 40° C.
J. The process of any one of the preceding embodiments, wherein the process is carried out in the absence of formamides and acetamides.
K. The process of any one of the preceding embodiments, wherein R is an alkyl or alkenyl group derived from lauric acid, myristic acid, palmitic acid, stearic acid, palm oil, palm kernel oil or coconut oil.
L. A process for preparing an N-acyl amino acid salt of formula (I)

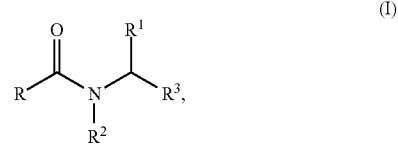

(I)

wherein
R is a linear or branched, saturated alkyl group having from 6 to 30 carbon atoms, or a linear or branched, mono- or polyunsaturated alkenyl group having from 6 to 30 carbon atoms,
$R^1$ is selected from the residues on the α-carbon of natural α-amino acids,
$R^2$ is H or an alkyl group with 1 to 4 carbon atoms,
$R^3$ is selected from COOQ and $CH_2$—$SO_3Q$, and
Q is a cation or a combination of more than one cation, wherein the process comprises the process for preparing a fatty acid chloride of formula R—COCl according any one of the preceding embodiments, further comprising
iii. reacting the fatty acid chloride of step ii. with a compound of formula (II)

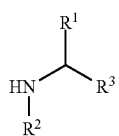

(II)

to form the N-acyl amino acid salt of formula (I), wherein step iii. is carried out in water, and in the presence of a base providing cations Q.

M. The process of embodiment L, wherein the compound of formula (II) is selected from the group consisting of natural and non-natural amino acids, and amino ethane sulfonic acids.

N. The process of any one of embodiments L or M, wherein the compound of formula (II) is glycine, taurine or N-methyl taurine.

O. The process of any one of embodiments L to N, wherein the compound of formula (II) is the same as the catalyst used in step ii.

P. The process of any one of embodiments L to O, wherein the process is carried out in the absence of formamides and acetamides.

Q. The process of any one of embodiments L to P, wherein R is an alkyl or alkenyl group derived from lauric acid, myristic acid, palmitic acid, stearic acid, palm oil, palm kernel oil or coconut oil.

R. The process of any one of embodiments L to Q, wherein Q is $Na^+$, $K^+$, or a combination thereof.

S. The process of any one of embodiments L to R, wherein $R^1$ is H.

T. The process of any one of embodiments L to S, wherein $R^2$ is H.

U. The process of any one of embodiments L to T, wherein $R^3$ is COOQ.

V. The process of any one of embodiments L to U, wherein $R^1$ is H, $R^2$ is H, and $R^3$ is COOQ.

W. The process of any one of embodiments L to V, wherein the base used in step iii. is sodium hydroxide, potassium hydroxide, or a combination thereof.

X. The process of any one of embodiments L to W, wherein the molar ratio of fatty acid chloride to compound of formula (II) is in the range of from 1:1 to 1:1.1.

Y. The process of any one of embodiments L to X, wherein step iii. is carried out at pH 9-13.

Z. The process of any one of embodiments L to Y, wherein step iii. is carried out at temperature of 25 to 50° C.

AA. A process for preparing a personal care composition comprising
A) preparing an N-acyl amino acid salt of formula (I) according to any of embodiments L to Z; and
B) formulating the N-acyl amino acid salt of formula (I) into a composition comprising a cosmetically acceptable carrier and at least one cosmetic benefit agent to form a personal care composition.

BB. An N-acyl amino acid salt of formula (I) obtained according to the process of any one of embodiments L to Z.

The invention claimed is:

1. A process for preparing a fatty acid chloride of formula R—COCl, wherein R is a linear or branched, saturated alkyl group having from 6 to 30 carbon atoms, or a linear or branched, mono- or polyunsaturated alkenyl group having from 6 to 30 carbon atoms,
wherein the process comprises the steps of
i) providing a fatty acid of formula R—COOH, and
ii) reacting the fatty acid of step i) with phosphorous trichloride, thionyl chloride or phosgene, in the presence of a catalyst to form a fatty acid chloride of formula R—COCl, wherein the catalyst is an amine, and wherein the amine is selected from the group consisting of amino acids and amino ethane sulfonic acids.

2. The process of claim 1, wherein the amine is glycine, taurine or N-methyl taurine.

3. The process of claim 1, wherein step ii) is carried out with an excess of phosphorous trichloride, thionyl chloride or phosgene, of at least 5%, based on the stoichiometric amount of fatty acid.

4. The process of claim 1, wherein step ii) is carried out with an excess of phosphorous trichloride, thionyl chloride or phosgene, of from 5 to 25%, based on the stoichiometric amount of fatty acid.

5. The process of claim 1, wherein step ii) is carried out with an excess of phosphorous trichloride, thionyl chloride or phosgene, of from 7 to 10%, based on the stoichiometric amount of fatty acid.

6. The process of claim 1, wherein step ii) is carried out in the presence of from 0.5 to 10 wt.-% of catalyst, based on the total weight of the fatty acid.

7. The process of claim 1, wherein step ii) is carried out in the presence of from 2.5 to 3 wt.-% of catalyst, based on the total weight of the fatty acid.

8. The process of claim 1, wherein step ii) is carried out at a temperature of from 25 to 65° C.

9. The process of claim 1, wherein the process is carried out in the absence of formamides and acetamides.

10. The process of claim 1, wherein R is an alkyl or alkenyl group derived from lauric acid, myristic acid, palmitic acid, stearic acid, palm oil, palm kernel oil or coconut oil.

11. A process for preparing an N-acyl amino acid salt of formula (I)

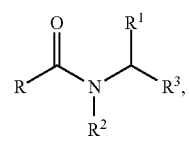

(I)

wherein
R is a linear or branched, saturated alkyl group having from 6 to 30 carbon atoms, or a linear or branched, mono- or polyunsaturated alkenyl group having from 6 to 30 carbon atoms,
$R^1$ is selected from the group consisting of the residues on the α-carbon of natural α-amino acids,
$R^2$ is H or an alkyl group with 1 to 4 carbon atoms,
$R^3$ is selected from the group consisting of COOQ and $CH_2$—$SO_3Q$, and
Q is a cation or a combination of more than one cation,
wherein the process comprises the steps of
  i) providing a fatty acid of formula R—COOH, wherein R is a linear or branched, saturated alkyl group having from 6 to 30 carbon atoms, or a linear or branched, mono- or polyunsaturated alkenyl group having from 6 to 30 carbon atoms,
  ii) reacting the fatty acid of step i) with phosphorous trichloride, thionyl chloride or phosgene, in the presence of a catalyst to form a fatty acid chloride of formula R—COCl, wherein the catalyst is an amine, and wherein the amine is selected from the group consisting of amino acids and amino ethane sulfonic acids, and
  iii) reacting the fatty acid chloride of step ii) with a compound of formula (II)

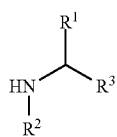
(II)

to form the N-acyl amino acid salt of formula (I), wherein step iii) is carried out in water, and in the presence of a base providing cations Q.

12. The process of claim 11, wherein the compound of formula (II) is selected from the group consisting of natural and non-natural amino acids, and amino ethane sulfonic acids.

13. The process of claim 11, wherein the compound of formula (II) is glycine, taurine or N-methyl taurine.

14. The process of claim 11, wherein the compound of formula (II) is the same as the catalyst used in step.

15. The process of claim 11, wherein the process is carried out in the absence of formamides and acetamides.

16. The process of claim 11, wherein R is an alkyl or alkenyl group derived from lauric acid, myristic acid, palmitic acid, stearic acid, palm oil, palm kernel oil or coconut oil.

17. The process of claim 11, wherein Q is $Na^+$, $K^+$, or a combination thereof.

18. The process of claim 11, wherein $R^1$ is H.

19. The process of claim 11, wherein $R^2$ is H.

20. The process of claim 11, wherein $R^3$ is COOQ.

21. The process of claim 11, wherein $R^1$ is H, $R^2$ is H, and $R^3$ is COOQ.

22. The process of claim 11, wherein the base used in step iii) is sodium hydroxide, potassium hydroxide, or a combination thereof.

23. The process of claim 11, wherein the molar ratio of fatty acid chloride to compound of formula (II) is in the range of from 1:1 to 1:1.1.

24. The process of claim 11, wherein step iii) is carried out at a pH of 9-13.

25. The process of claim 11, wherein step iii) is carried out at temperature of 25 to 50° C.

26. A process for preparing a personal care composition comprising
  A) preparing an N-acyl amino acid salt of formula (I) according to claim 11; and
  B) formulating the N-acyl amino acid salt of formula (I) into a composition comprising a cosmetically acceptable carrier and at least one cosmetic benefit agent to form a personal care composition.

\* \* \* \* \*